US009421382B2

United States Patent
Ebert et al.

(10) Patent No.: US 9,421,382 B2
(45) Date of Patent: Aug. 23, 2016

(54) METHOD AND APPARATUS FOR MONITORING OF PATIENT MEDICATION COMPLIANCE

(71) Applicant: Medtronic, Inc., Minneapolis, MN (US)

(72) Inventors: Michael J Ebert, Fridley, MN (US); Amy Thompson-Nauman, Coon Rapids, MN (US); Nathan A Grenz, Shoreview, MN (US); Rick D McVenes, Isanti, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/105,306

(22) Filed: Dec. 13, 2013

(65) Prior Publication Data

US 2015/0165213 A1 Jun. 18, 2015

(51) Int. Cl.
*A61N 1/00* (2006.01)
*A61N 1/37* (2006.01)
*A61N 1/372* (2006.01)

(52) U.S. Cl.
CPC ......... *A61N 1/3702* (2013.01); *A61N 1/37247* (2013.01); *A61N 1/37258* (2013.01); *A61N 1/37264* (2013.01)

(58) Field of Classification Search
CPC ... A61N 1/371; A61N 1/3712; A61N 1/3714
USPC .................................................. 607/28, 27, 9
See application file for complete search history.

(56) References Cited

U.S. PATENT DOCUMENTS

| | | |
|---|---|---|
| 4,374,382 A | 2/1983 | Markowitz |
| 5,117,824 A | 6/1992 | Keimel et al. |
| 5,545,186 A | 8/1996 | Olson et al. |
| 5,755,736 A | 5/1998 | Gillberg et al. |
| 6,434,428 B1 * | 8/2002 | Sloman et al. ............. 607/28 |
| 6,449,508 B1 | 9/2002 | Sheldon et al. |
| 7,414,534 B1 | 8/2008 | Kroll et al. |
| 7,440,804 B1 | 10/2008 | Min et al. |
| 7,616,111 B2 | 11/2009 | Covannon et al. |
| 7,752,189 B2 | 7/2010 | Yamashita |
| 7,876,228 B2 | 1/2011 | Kroll et al. |
| 7,945,461 B2 | 5/2011 | Sekura |
| 8,052,611 B2 | 11/2011 | Wariar et al. |
| 8,060,249 B2 | 11/2011 | Bear et al. |
| 8,092,224 B2 | 1/2012 | Walker et al. |
| 8,126,554 B2 | 2/2012 | Kane et al. |
| 8,150,709 B2 | 4/2012 | Miller et al. |
| 8,212,677 B2 | 7/2012 | Ferguson |
| 8,234,127 B2 | 7/2012 | Naik et al. |
| 8,262,394 B2 | 9/2012 | Walker et al. |
| 8,269,635 B2 | 9/2012 | Kroll et al. |
| 8,269,636 B2 | 9/2012 | Kroll et al. |
| 8,321,013 B2 | 11/2012 | Darvish et al. |
| 8,401,627 B1 | 3/2013 | Farazi et al. |
| 8,428,729 B2 | 4/2013 | Schwartz et al. |
| 8,564,432 B2 | 10/2013 | Covannon et al. |
| 9,131,865 B2 | 9/2015 | Thompson-Nauman et al. |
| 9,138,157 B2 | 9/2015 | Thompson-Nauman et al. |

(Continued)

*Primary Examiner* — Amanda Patton
*Assistant Examiner* — Philip Edwards
(74) *Attorney, Agent, or Firm* — Carol F. Barry (57) ABSTRACT

A method and medical device for monitoring patient medication compliance that includes a plurality of electrodes to deliver a pacing therapy and a processor configured to determine a pacing threshold in response to the delivered pacing therapy, determine whether there is a change in the pacing threshold, and determine patient medication compliance in response to the determined changes.

21 Claims, 8 Drawing Sheets

(56) References Cited

U.S. PATENT DOCUMENTS

| | | |
|---|---|---|
| 2004/0088019 A1* | 5/2004 | Rueter et al. .................... 607/27 |
| 2004/0172075 A1* | 9/2004 | Shafer et al. ..................... 607/9 |
| 2006/0167365 A1 | 7/2006 | Bharmi |
| 2006/0217771 A1 | 9/2006 | Soykan et al. |
| 2009/0234211 A1 | 9/2009 | Li et al. |
| 2012/0197231 A1 | 8/2012 | Kane et al. |
| 2012/0245960 A1 | 9/2012 | Bartholomew, III et al. |
| 2012/0277546 A1 | 11/2012 | Soykan et al. |
| 2012/0316897 A1 | 12/2012 | Hanina et al. |
| 2013/0073303 A1 | 3/2013 | Hsu |
| 2013/0090937 A1 | 4/2013 | Wright |
| 2013/0218588 A1 | 8/2013 | Kehr et al. |
| 2013/0274623 A1 | 10/2013 | Zhang |

\* cited by examiner

METHOD AND APPARATUS FOR MONITORING OF PATIENT MEDICATION COMPLIANCE

RELATED APPLICATION

Cross-reference is hereby made to commonly assigned U.S. patent application Ser. No. 14/105,314, filed on even date herewith entitled "METHOD AND APPARATUS FOR MONITORING OF PATIENT MEDICATION COMPLIANCE", and incorporated by reference in its entirety.

FIELD OF THE DISCLOSURE

This disclosure relates generally to medical devices and, in particular, to a method and apparatus for monitoring compliance of a patient medication regimen through monitoring of cardiac function by an implantable medical device.

BACKGROUND

Medications are prescribed to millions of patients to address a wide variety of medical conditions. It is often difficult, however, for physicians to ensure that appropriate dosages of prescribed medications are actually taken by their patients and at the appropriate times. Patients may intentionally or unintentionally fail to take prescribed drugs, or the prescribed drug may be taken by the patient, but with an incorrect dosage level. For many medical conditions, including serious heart conditions such as congestive heart failure (CHF), failure to take the prescribed dosage of the drug in a timely manner can have severe adverse consequences. One approach for monitoring compliance of patient ingestion of medication involves the use of radio frequency identification tags that are typically implanted, either by being ingested or inserted under the skin. Such devices tend to be cost prohibitive since they require a great deal of development to ensure against damage, either of the device or to the patient resulting from the ingestion of the device by the patient. Therefore, what is needed is a method and apparatus for automatically monitoring prescription drug intake to enable a physician to determine whether a patient has taken their medication, whether the medication has been taken at the proper dosage and/or at the proper time of day, or whether the patient has only taken prescribed medication sporadically.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

A medical device according to the present invention may include one or more of the features, structures, methods, or combinations thereof described herein below. For example, a status monitor, cardiac monitor, cardiac stimulator, or other type of implantable or patient-external medical device may be implemented to include one or more of the advantageous features and/or processes described below. It is intended that such a monitor, stimulator, or other external, implanted or partially implanted device need not include all of the features described herein, but may be implemented to include selected features that provide for useful structures and/or functionality. Such a device may be implemented to provide a variety of therapeutic or diagnostic functions.

Figure 1:
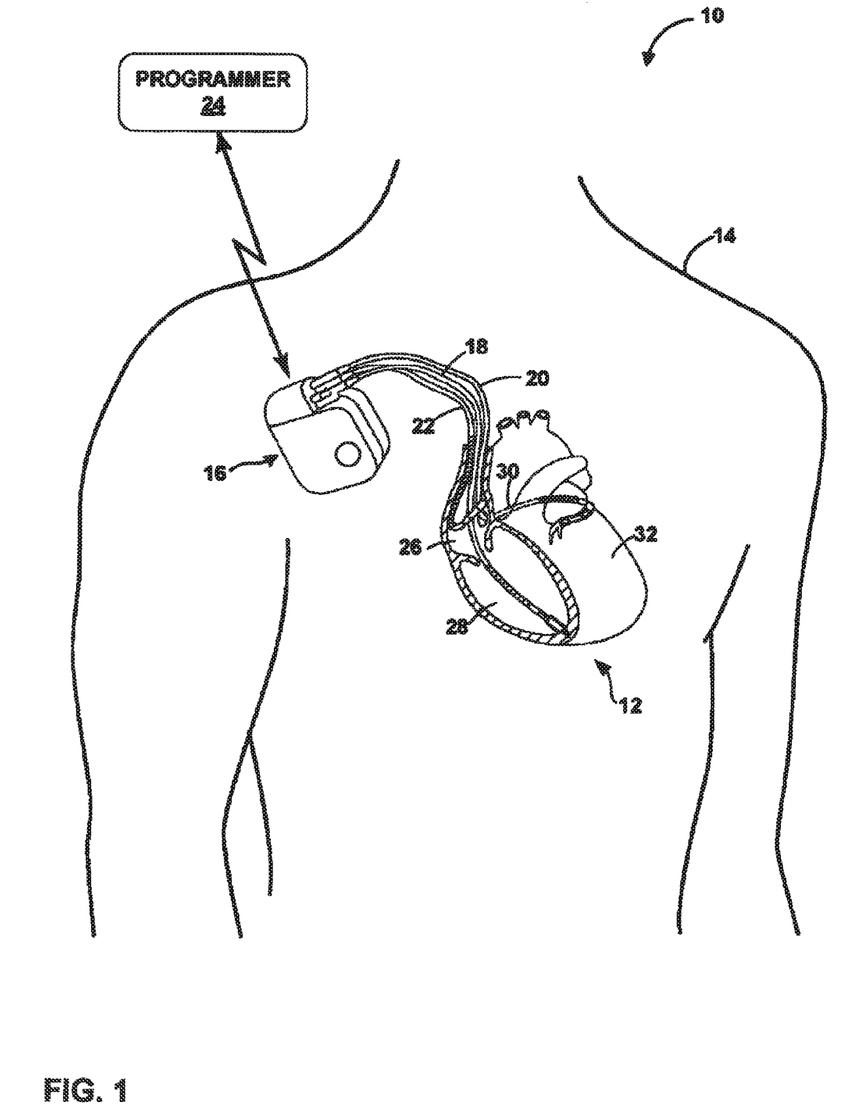
FIG. 1 is a functional block diagram of an exemplary medical device for monitoring cardiac function according to an embodiment of the present disclosure.

FIG. 1 is a conceptual diagram illustrating an exemplary system 10 for monitoring cardiac function according to an embodiment of the present disclosure. System 10 includes implantable medical device (IMD) 16, which is connected to leads 18, 20, and 22 and is communicatively coupled to a programmer 24. IMD 16 senses electrical signals attendant to the depolarization and repolarization of heart 12, e.g., a cardiac electrogram (EGM), via electrodes on one or more leads 18, 20 and 22 or the housing of IMD 16. IMD 16 may also deliver therapy in the form of electrical signals to heart 12 via electrodes located on one or more leads 18, 20 and 22 or a housing of IMD 16, the therapy may be pacing, cardioversion and/or defibrillation pulses.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, programmer 24 takes the form of a handheld computing device, computer workstation or networked computing device that includes a user interface for presenting information to and receiving input from a user. A user, such as a physician, technician, surgeon, electrophysiologist, or other clinician, may interact with programmer 24 to retrieve physiological or diagnostic information from IMD 16. A user may also interact with programmer 24 to program IMD 16, e.g., select values for operational parameters of the IMD.

IMD 16 and programmer 24 may communicate via wireless communication using any techniques known in the art. Examples of communication techniques may include, for example, low frequency or radiofrequency (RF) telemetry. Other techniques are also contemplated. In some examples, programmer 24 may include a programming head that may be placed proximate to the patient's body near the IMD 16 implant site in order to improve the quality or security of communication between IMD 16 and programmer 24. In some examples, programmer 24 may be located remotely from IMD 16, and communicate with IMD 16 via a network. Programmer 24 may also communicate with one or more other external devices using a number of known communication techniques, both wired and wireless.

Figure 2:
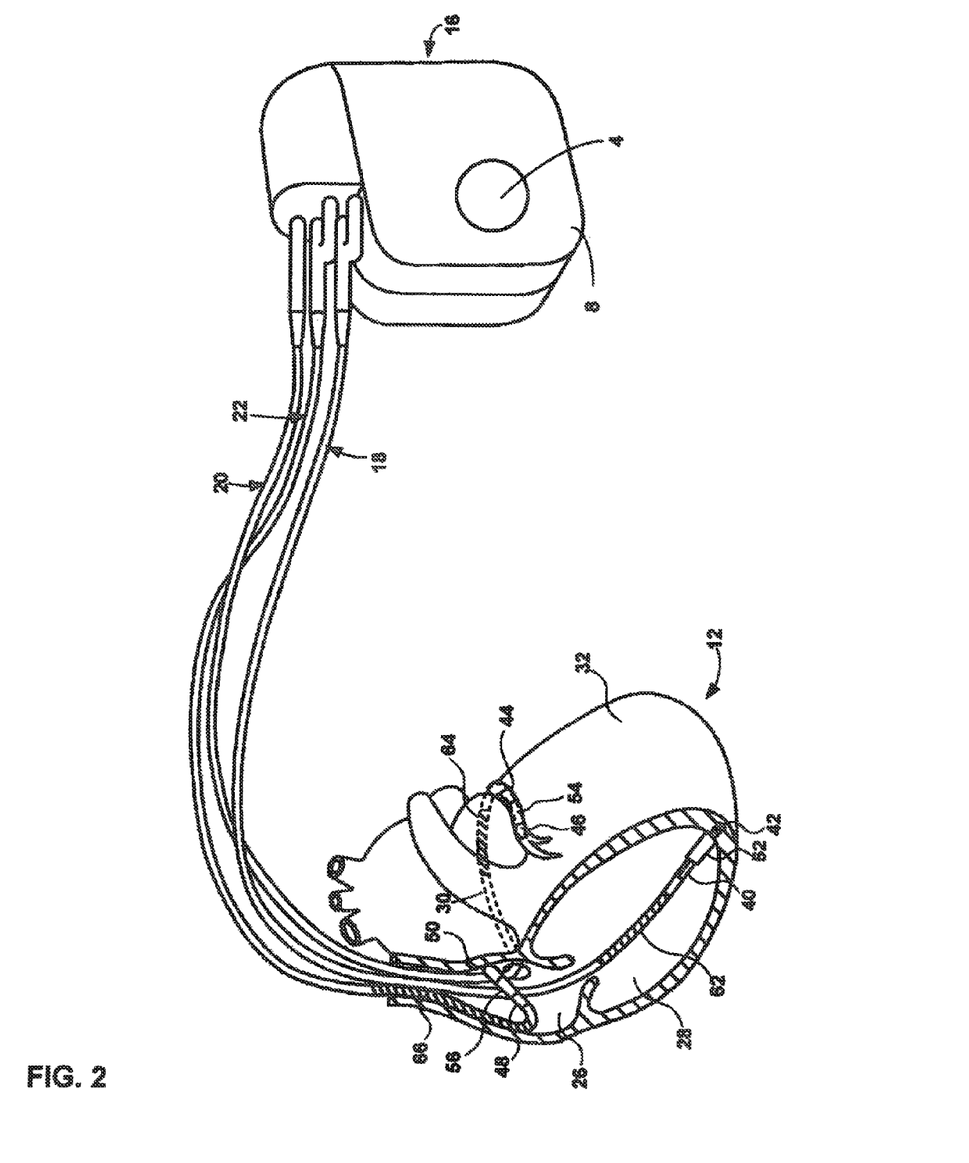
FIG. 2 is a conceptual diagram of the medical device of FIG. 1 according to an embodiment of the present disclosure.

FIG. 2 is a conceptual diagram illustrating IMD 16 and leads 18, 20 and 22 of system 10 in greater detail. In the illustrated example, bipolar electrodes 40 and 42 are located adjacent to a distal end of lead 18. In addition, bipolar electrodes 44 and 46 are located adjacent to a distal end of lead 20, and bipolar electrodes 48 and 50 are located adjacent to a distal end of lead 22. In alternative embodiments, not shown in FIG. 2, one or more of leads 18, 20 and 22, e.g., left-ventricular lead 20, may include quadrapole electrodes located adjacent to a distal end of the lead.

In the illustrated example, electrodes 40, 44 and 48 take the form of ring electrodes, and electrodes 42, 46 and 50 may take the form of extendable helix tip electrodes mounted retractably within insulative electrode heads 52, 54 and 56, respectively. Leads 18, 20, 22 also include elongated electrodes 62, 64, 66, respectively, which may take the form of a coil. In some examples, each of electrodes 40, 42, 44, 46, 48, 50, 62, 64 and 66 is electrically coupled to a respective conductor within the lead body of its associated lead 18, 20, 22 and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8.

As described in further detail with reference to FIG. 3, housing 8 encloses a signal generator that generates therapeutic stimulation, such as cardiac pacing, cardioverison and defibrillation pulses, as well as a sensing module for sensing electrical signals attendant to the depolarization and repolarization of heart 12. IMD 16 senses electrical signals attendant to the depolarization and repolarization of heart 12 via electrodes 4, 40, 42, 44, 46, 48, 50, 62, 64 and 66. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intercardiac leads 18, 20 and 22, system 10 may include one or more epicardial or subcutaneous leads not positioned within the heart. In some examples, system 10 may include an additional lead that carries an acoustic sensor positioned such that signals generated by the acoustic sensor include respiratory sounds in response to a cough or diaphragm movement.

Furthermore, in some examples, IMD 16 need not be coupled to any leads, need not provide electrical stimulation or other therapy, and/or need not sense electrical cardiac signals. In some examples, the techniques described herein may be implemented in a leadless monitoring device, such as a Reveal® insertable monitor available from Medtronic, Inc. of Minneapolis, Minn. Such a device may be configured to include additional sensors, such as an acoustic sensor and/or, an activity sensor, and provide the functionality described herein with respect to IMD 16.

Figure 3:
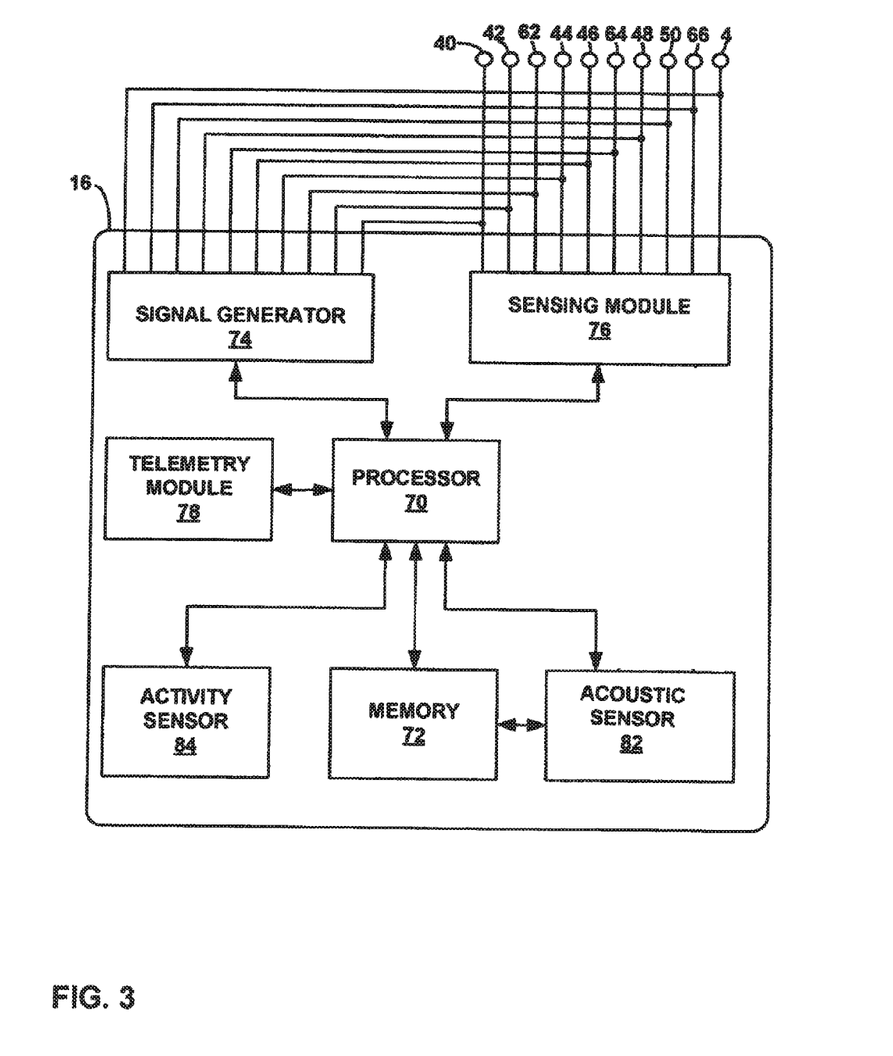
FIG. 3 is an exemplary functional block diagram of an exemplary configuration of the medical device of FIG. 1 according to an embodiment of the present disclosure.

FIG. 3 is a block diagram illustrating an example configuration of IMD 16. In the illustrated example, IMD 16 includes a processor 70, memory 72, signal generator 74, sensing module 76, telemetry module 78, acoustic sensor 82, and activity sensor 84. Memory 72 includes computer-readable instructions that, when executed by processor 70, cause IMD 16 and processor 70 to perform various functions attributed to IMD 16 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 to deliver stimulation therapy to heart 12 of patient 14 according to a selected one or more of therapy programs or parameters, which may be stored in memory 72. As an example, processor 70 may control signal generator 74 to deliver electrical pulses with the amplitudes, pulse widths, frequency, or electrode polarities specified by the selected one or more therapy programs or parameters.

Signal generator 74 is configured to generate and deliver electrical stimulation therapy to patient 14. As shown in FIG. 3, signal generator 74 is electrically coupled to electrodes 4, 40, 42, 44, 46, 48, 50, 62, 64 and 66, e.g., via conductors of the respective leads 18, 20, and 22 and, in the case of housing electrode 4, within housing 8. For example, signal generator 74 may deliver pacing, defibrillation or cardioversion pulses to heart 12 via at least two of electrodes 4, 40, 42, 44, 46, 48, 50, 62, 64 and 66. In some examples, signal generator 74 delivers stimulation in the form of signals other than pulses such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 4, 40, 42, 44, 46 48, 50, 62, 64, and 66. Sensing module 76 may also include a switch module which processor 70 controls to select which of the available electrodes are used to sense the heart activity, depending upon which electrode combination is used in the current sensing configuration.

Sensing module 76 may include one or more detection channels, each of which may comprise an amplifier. The detection channels may be used to sense the cardiac signals. Some detection channels may detect events, such as R-waves or P-waves, and provide indications of the occurrences of such events to processor 70. One or more other detection channels may provide the signals to an analog-to-digital converter, for conversion into a digital signal for processing or analysis by processor 70.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 76 or processor 70. Processor 70 may analyze the digitized version of signals from the wide band channel. Processor 70 may employ digital signal analysis techniques to characterize the digitized signals from the wide band channel to, for example, detect and classify the patient's heart rhythm.

Processor 70 may detect and classify the patient's heart rhythm based on the cardiac electrical signals sensed by sensing module 76 employing any of the numerous signal processing methodologies known in the art. For example, processor 70 may maintain escape interval counters that may be reset upon sensing of R-waves by sensing module 76. The value of the count present in the escape interval counters when reset by sensed depolarizations may be used by processor 70 to measure the durations of R-R intervals, which are measurements that may be stored in memory 72. Processor 70 may use the count in the interval counters to detect a tachyarrhythmia, such as ventricular fibrillation or ventricular tachycardia. A portion of memory 72 may be configured as a plurality of recirculating buffers, capable of holding series of measured intervals, which may be analyzed by processor 70 to determine whether the patient's heart 12 is presently exhibiting atrial or ventricular tachyarrhythmia.

In some examples, processor 70 may determine that tachyarrhythmia has occurred by identification of shortened R-R interval lengths. Generally, processor 70 detects tachycardia when the interval length falls below 360 milliseconds (ms) and fibrillation when the interval length falls below 320 ms. These interval lengths are merely examples, and a user may define the interval lengths as desired, which may then be stored within memory 72. This interval length may need to be detected for a certain number of consecutive cycles, for a certain percentage of cycles within a running window, or a running average for a certain number of cardiac cycles, as examples.

In some examples, an arrhythmia detection method may include any suitable tachyarrhythmia detection algorithms. In one example, processor 70 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 70 in some examples. For example, EGM morphology may be considered in addition to or instead of interval length for detecting tachyarrhythmias.

Generally, processor 70 detects a treatable tachyarrhythmia, such as VF, based on the EGM, e.g., the R-R intervals and/or morphology of the EGM, and selects a therapy to deliver to terminate the tachyarrhythmia, such as a defibrillation pulse of a specified magnitude. The detection of the tachyarrhythmia may include a number of phases or steps prior to delivery of the therapy, such as first phase, sometimes referred to as detection, in which a number of consecutive or proximate R-R intervals satisfies a first number of intervals to detect (NID) criterion, a second phase, sometimes referred to as confirmation, in which a number of consecutive or proximate R-R intervals satisfies a second, more restrictive NID criterion. Tachyarrhythmia detection may also include confirmation based on EGM morphology or other sensors subsequent to or during the second phase. Again, in some cases, processor 70 may mistakenly classify the patient's heart rhythm as a treatable tachyarrhythmia, e.g., as a result of a noisy EGM.

IMD 16 may also include one or more additional sensors, such as an acoustic sensor 82 and/or an activity sensor 84, for example. Acoustic sensor 82 generates an electrical signal based on sound or vibration, e.g., sensed heart sounds of patient 14, and may be implemented as a piezoelectric sensor, a microphone, an accelerometer, or other type of acoustical sensor. In some examples, acoustic sensor 82 may comprise more than one sensor. For example, acoustic sensor 82 may include multiple accelerometer devices. Activity sensor 84 may also comprise one or more accelerometers. Information obtained from acoustic sensor 82 and/or activity sensor 84 may be used to provide additional information, such as a risk assessment with regard to worsening heart failure or ventricular tachycardia and/or fibrillation.

In the illustrated example of FIG. 3, acoustic sensor 82 is enclosed within housing 8 of IMD 16. In some examples, acoustic sensor 82 may be formed integrally with an outer surface of housing 8. For example, acoustic sensor 82 may be a piezoelectric sensor attached to the outer surface of housing 8. In some examples, acoustic sensor 82 is located on a lead that is coupled to IMD 16 or may be implemented in a remote sensor that wirelessly communicates with IMD 16 via telemetry module 78. In any case, acoustic sensor 82 is electrically or wirelessly coupled to circuitry contained within housing 8 of IMD 16.

Activity sensor 84 may, for example, take the form of one or more accelerometers, or any other sensor known in the art for detecting activity, e.g., body movements or footfalls, or posture. In some examples, activity sensor 84 may comprise a three-axis accelerometer. In some examples, acoustic sensor 82 and activity sensor 84 may comprise one or more common accelerometers. Processor 70 may determine an activity level count at regular intervals based on the signal(s) from activity sensor 84. In some examples, processor 70 may determine a running average activity count based on the information provided by activity sensor 84. For example, the activity count may be calculated over a 1 second interval and the processor 70 may update the activity level count at a 1 second interval. A method of determining activity count from an accelerometer sensor is described in U.S. Pat. No. 6,449,508, to Sheldon et al, entitled, "ACCELEROMETER COUNT CALCULATION FOR ACTIVITY SIGNAL FOR AN IMPLANTABLE MEDICAL DEVICE," issued Sep. 10, 2002, and incorporated herein by reference in its entirety.

Activity sensor 84 may be located outside of the housing 8 of IMD 16. Activity sensor 84 may be located in such a manner to pick up chest motion, for example. Activity sensor 84 may be located on a lead that is coupled to IMD 16 or may be implemented in a remote sensor that wirelessly communicates with IMD 16 via telemetry module 78. In any case, activity sensor 84 is electrically or wirelessly coupled to circuitry contained within housing 8 of IMD 16.

Telemetry module 78 includes any suitable hardware, firmware, software or any combination thereof for communicating with another device, such as programmer 24 (FIG. 1). Under the control of processor 70, telemetry module 78 may receive downlink telemetry from and send uplink telemetry to programmer 24 with the aid of an antenna, which may be internal and/or external. In some examples, processor 70 may transmit cardiac signals, e.g., ECG or EGM signals, produced by sensing module 76 and/or signals by acoustic sensor 82 to programmer 24. Processor 70 may also generate and store marker codes indicative of different cardiac or other physiological events detected by sensing module 76 and transmit the marker codes to programmer 24. An example IMD with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. Information which processor 70 may transmit to programmer 24 via telemetry module 78 may also include an indication of a change in disease state of the heart, an indication of a change in heart response to the therapy provided or an indication that the heart continues to response in the same (or similar) manner to the therapy provided, the indications based on heart sounds and/or EGM signals. Such information may be included as part of a marker channel with an EGM.

Figure 4:
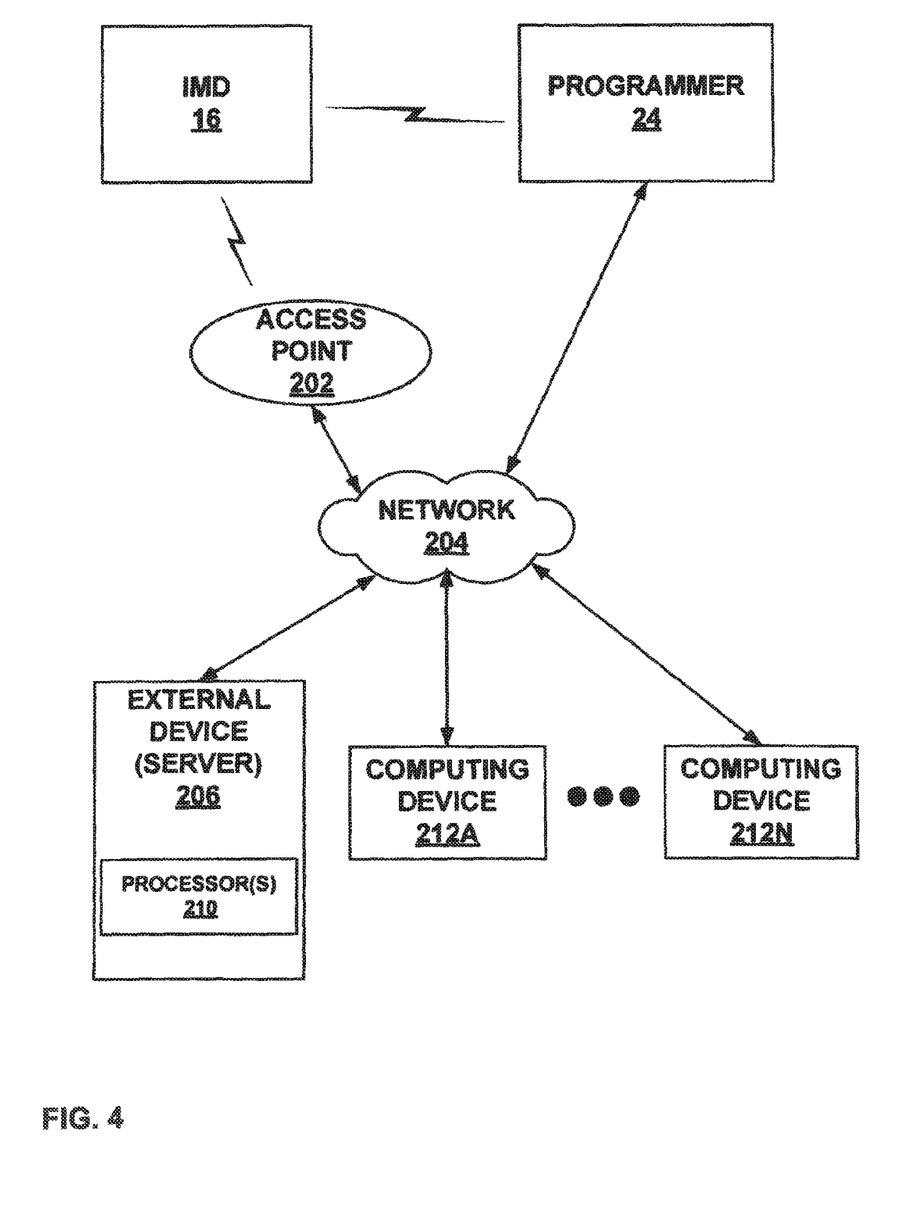
FIG. 4 is an exemplary block diagram illustrating an example system that includes an external device, such as a server, and one or more computing devices coupled to the medical device and programmer shown in FIG. 1 via a network.

FIG. 4 is an exemplary block diagram illustrating an example system that includes an external device, such as a server 206, and one or more computing devices 212A-212N that are coupled to the IMD 16 and programmer 24 shown in FIG. 1 via a network 204. Network 204 may be generally used to transmit diagnostic information (e.g., activity level and/or heart sounds) from an IMD 16 to a remote external computing device. In some examples, the acoustic and/or EGM signals may be transmitted to an external device for processing.

In some examples, the information transmitted by IMD 16 may allow a clinician or other healthcare professional to monitor patient 14 remotely. In some examples, IMD 16 may use its telemetry module 78 to communicate with programmer 24 via a first wireless connection, and to communicate with an access point 202 via a second wireless connection, e.g., at different times. In the example of FIG. 4, access point 202, programmer 24, server 206, and computing devices 212A-212N are interconnected, and able to communicate with each other, through network 204. In some cases, one or more of access point 202, programmer 24, server 206, and computing devices 212A-3212 N may be coupled to network 204 via one or more wireless connections. IMD 16, programmer 24, server 206, and computing devices 212A-212N may each comprise one or more processors, such as one or more microprocessors, DSPs, ASICs, FPGAs, programmable logic circuitry, or the like, that may perform various functions and operations, such as those described herein.

Access point 202 may comprise a device that connects to network 204 via any of a variety of connections, such as telephone dial-up, digital subscriber line (DSL), or cable modem connections. In other examples, access point 202 may be coupled to network 204 through different forms of connections, including wired or wireless connections. In some examples, access point 202 may be co-located with patient 14 and may comprise one or more programming units and/or computing devices (e.g., one or more monitoring units) that may perform various functions and operations described herein. For example, access point 202 may include a home-monitoring unit that is co-located with patient 14 and that may monitor the activity of IMD 16. In some examples, server 206 or computing devices 212 may control or perform any of the various functions or operations described herein, e.g., determine, based on the sensed cardiac signal, whether homeostasis variations, such as hypokalemia, are occurring, as described below in detail.

In some cases, server 206 may be configured to provide a secure storage site for archival of diagnostic information (e.g., attendant circumstances such as patient posture, activity level, or heart sounds) that has been collected and generated from IMD 16 and/or programmer 24. Network 204 may comprise a local area network, wide area network, or global network, such as the Internet. In some cases, programmer 24 or server 206 may assemble homeostasis variations information in web pages or other documents for viewing by trained professionals, such as clinicians, via viewing terminals associated with computing devices 212. The system of FIG. 4 may be implemented, in some aspects, with general network technology and functionality similar to that provided by the Medtronic CareLink® Network developed by Medtronic, Inc., of Minneapolis, Minn.

Figure 5:
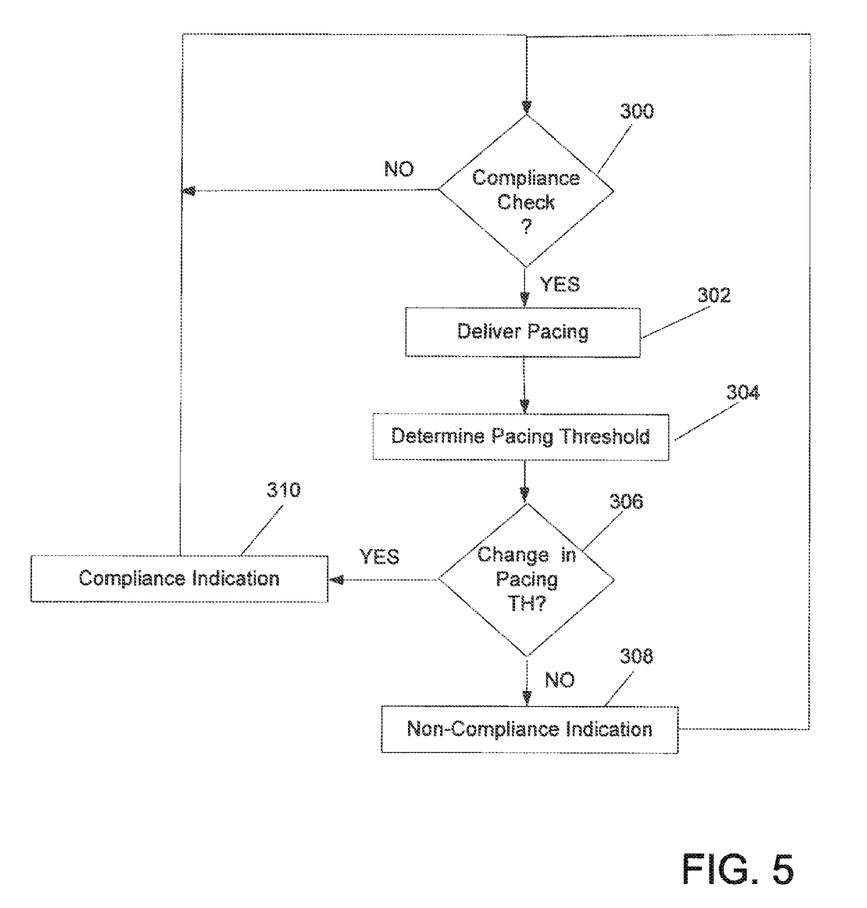
FIG. 5 is a flowchart of an exemplary method for monitoring compliance of a patient medication regimen in a medical device according to an embodiment of the present disclosure.

FIG. 5 is a flowchart of an exemplary method, according to an embodiment of the present disclosure, for monitoring compliance of a patient medication regimen in a medical device. Certain medications, such as anti-arrhythmic medications, for example, are frequently prescribed for a patient experiencing symptoms of heart failure. Other, non-anti-arrhythmic medications may also be prescribed, such as corticosteroids, for example. Typically, in order to be most effective, these medications must be ingested by the patient at certain times and at a specific number of times per day, which can vary depending on the specific prescribed medication involved. Therefore, as illustrated in FIG. 5, during monitoring of the device for patient compliance, in order to determine whether to initiate the determination of whether the patient has been compliant with ingestion of medication, the device determines whether it is time to perform the compliance check, Block 300. For example, depending on the type of each medication prescribed for a specific patient, the number of doses per day and the prescribed times for ingestion can typically be either a single dosage taken once per day in the early morning, or more than one dose per day, such as once in the morning and once later in the day, for example. Certain medications, such as anti-arrhythmic medications, cause an increase in the pacing threshold associated with an implantable device to occur when ingested by the patient, while others, such as corticosteroids, for example, cause a decrease in the pacing threshold associated with an implantable device to occur when ingested by the patient.

During the compliance check, YES in Block 300, the device delivers pacing therapy, Block 302, determines a current pacing therapy threshold, Block 304, and based on the current pacing therapy threshold, determines whether there has been a change in the pacing threshold, Block 306. For example, the device may be utilized to determine whether the patient is compliant in ingesting an anti-arrhythmic medication, such as amiodarone, in which case the device determines whether there is an increase in the pacing threshold, Block 306. According to another embodiment, if the device is attempting to determine patient compliance in ingesting a corticosteroid, the device determines whether there is a decrease in the pacing threshold, Block 306. In order to determine whether changes in the pacing threshold are occurring in Block 306, the device determines whether there is either an increase or a decrease in the pacing threshold by comparing the current determined pacing therapy threshold to a prior determined pacing threshold. According to one embodiment, the device determines that a change in the pacing threshold occurs if there is a one-step change in the current adjusted pacing threshold from a prior adjusted pacing threshold determination. According to one embodiment, a one-step increase or decrease in the pacing threshold corresponds to an increase of approximately one tenth of a volt, so that, for example, an increase from 0.1 volts to 0.2 volts would correspond to a one-step increase and a decrease from 0.2 volts to 0.1 volts would correspond to a one-step decrease.

During monitoring of compliance for ingestion of amiodarone, for example, if the pacing threshold has not increased, i.e., the current pacing threshold is not greater than the previous determined pacing threshold, NO in Block 306, the device determines the patient to be non-compliant, Block 308, and a non-compliant indication is generated that is stored, and/or causes an alert to be generated. If the pacing threshold has increased, i.e., the current pacing threshold is greater than the previous determined pacing threshold, YES in Block 306, the device determines the patient to be compliant, Block 310, and waits for the next compliance check, Block 300, to be scheduled to occur, and the process is repeated. An indication that the patient was determined to be either compliant or non-compliant may be stored for later review by the clinical personnel. According to one embodiment, if the patient is determined to be non-compliant, an alert may be generated to alert either of the patient, the attending medical personnel, or both, that the patient has been non-compliant. In some instances, once a patient has been determined to be noncompliant, it may be desirable to determine whether the patient did not ingest the dosage at any time during the day or ingested the medication at a time of the day inconsistent with the prescribed dosage time. For example, if the dosage is intended to be ingested at 10 am, but was ingested by the patient at 3 pm. Therefore, according to one embodiment, once the patient is determined to be noncompliant and an alert has been generated, the device may determine that a follow up compliance check is to be determined, Block 300, after a predetermined time period subsequent to delivery of the alert has expired. For example, if the medication is intended to be ingested at 10 am, but the patient is determined to be noncompliant and therefore the alert is generated, the device may determine that a follow-up compliance check should be performed, YES in Block 300, after a predetermined period of time, such as five hours, for example, subsequent to delivery of the alert. In another example, it may be desirable to determine whether the patient ingested the medication in response to having received the alert as a reminder. For example, if the medication is intended to be ingested at 10 am, but the patient is determined to be noncompliant and therefore the alert is generated, the device may determine that a follow-up compliance check should be performed, YES in Block 300, after a shorter period of time, such as one hour or less, for example, subsequent to delivery of the alert.

Similarly, during monitoring of compliance for ingestion of corticosteroid, for example, if the pacing threshold has not decreased, i.e., the current pacing threshold is not less than the previous determined pacing threshold, NO in Block 306, the device determines the patient non-compliant, Block 308, and a non-compliant indication is generated that is stored, and/or causes an alert to be generated. If the pacing threshold has decreased, i.e., the current pacing threshold is less than the previous determined pacing threshold, YES in Block 306, the device determines the patient to be compliant and waits for the next compliance check, Block 300, to be scheduled to occur, and the process is repeated. In addition, an indication that the patient was determined to be either of compliant or non-compliant may be stored for later review by the clinical personnel. According to one embodiment, if the patient is determined to be non-compliant, an alert may be generated to alert either one of the patient, the attending medical personnel, or both, that the patient has been non-compliant. If an alert is generated to alert the patient, a determination may be made as to whether the patient complies after the alert is generated, as described above.

Figure 6:
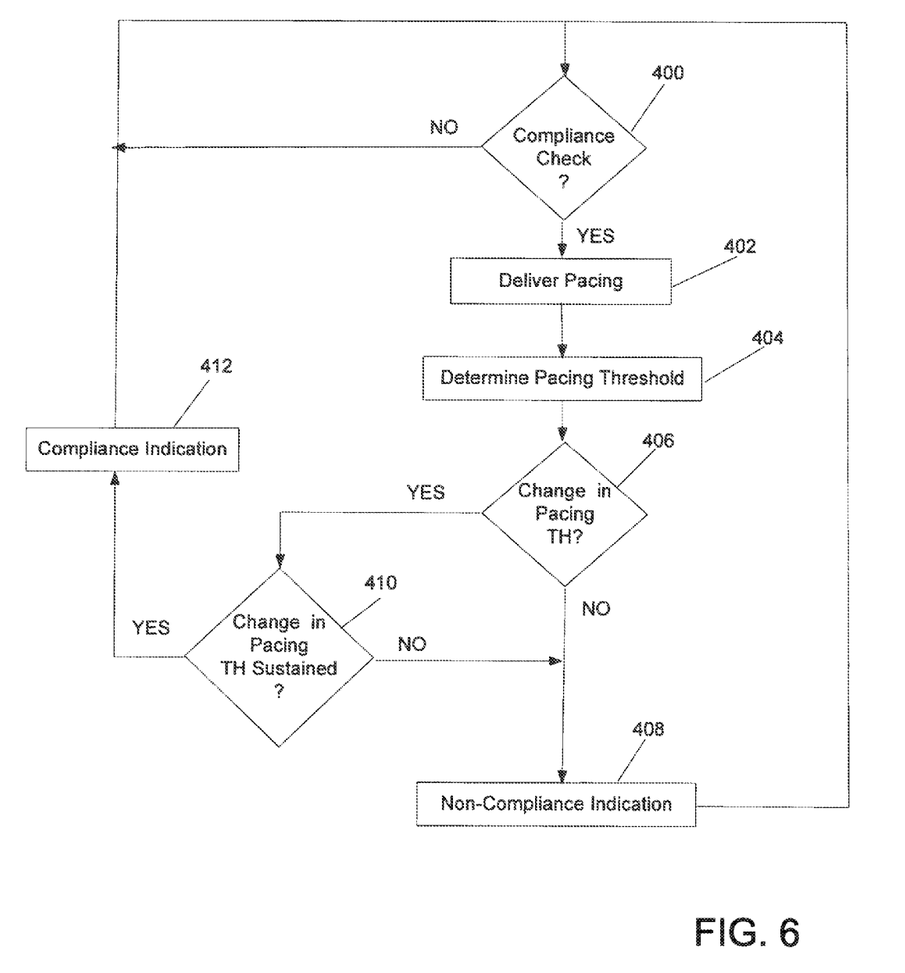
FIG. 6 is a flowchart of an exemplary method for monitoring compliance of a patient medication regimen in a medical device according to an embodiment of the present disclosure.

FIG. 6 is a flowchart of an exemplary method, according to an embodiment of the present disclosure, for monitoring compliance of a patient medication regimen in a medical device. As illustrated in FIG. 6, during monitoring of the device for patient compliance, in order to determine whether to initiate the determination of whether the patient has been compliant with ingestion of medication, the device determines whether it is time to perform the compliance check, Block 400, as described above. Once the compliance check is initiated, YES in Block 400, the device delivers pacing therapy, Block 402, determines a current pacing therapy threshold, Block 404, and based on the current pacing therapy threshold, determines whether there has been a change in the pacing threshold, Block 406. For example, if the device is attempting to determine patient compliance in ingesting amiodarone, the device determines whether there is an increase in the pacing threshold, Block 406. According to another embodiment, if the device is attempting to determine patient compliance in ingesting an ace inhibitor, the device determines whether there is a decrease in the pacing threshold, Block 406.

In order to determine whether changes in the pacing threshold are occurring in Block 406, the device determines whether there is either an increase or a decrease in the pacing threshold by comparing the current determined pacing therapy threshold to a prior determined pacing threshold. According to one embodiment, the device determines that a change in the pacing threshold occurs if there is a one-step change in the current adjusted pacing threshold from a prior adjusted pacing threshold determination. According to one embodiment, a one-step increase or decrease in the pacing threshold corresponds to a change of approximately one tenth of a volt, so that, for example, an increase from 0.1 volts to 0.2 volts would correspond to a one-step increase and a decrease from 0.2 volts to 0.1 volts would correspond to a one-step decrease.

During monitoring of compliance for ingestion of an amiodarone, for example, if the pacing threshold has not increased, i.e., the current pacing threshold is not greater than the previous determined pacing threshold, NO in Block 406, the device determines the patient non-compliant, Block 408, and a non-compliant indication is generated that is stored, and/or causes an alert to be generated. If an alert is generated to alert the patient, a determination may be made as to whether the patient complies after the alert is generated, as described above. If the pacing threshold has increased, i.e., the current pacing threshold is greater than the previous determined pacing threshold, YES in Block 406, the device determines whether the change in pacing threshold has been sustained for a predetermined period of time, Block 410.

Typically, if the patient has been compliant in ingesting medication, the ingestion of the medication will tend to cause the change in the pacing threshold to occur and remain greater than the pacing threshold of Block 406 for a prolonged period of time, such as 1-3 hours, for example. Therefore, once the device determines the change in pacing threshold to have occurred, YES in Block 406, the device determines whether the change in pacing threshold was sustained for a predetermined period of time, such as three hours, for example, Block 410. If the change in pacing threshold is not sustained, i.e., the pacing threshold is determined not to be greater than the pacing threshold for the predetermined period of time, NO in Block 410, the device determines the patient non-compliant, Block 408, and a non-compliant indication is generated that is stored, and/or causes an alert to be generated. If an alert is generated to alert the patient, a determination may be made as to whether the patient complies after the alert is generated, as described above.

If the change in pacing threshold is sustained, i.e., the pacing threshold is determined to be greater than the pacing threshold for the predetermined period of time, YES in Block 410, the device determines the patient to be compliant, Block 410, and waits for the next compliance check, Block 400, to be scheduled to occur, and the process is repeated. An indication that the patient was determined to be either compliant or non-compliant may be stored for later review by the clinical personnel. According to one embodiment, if the patient is determined to be non-compliant, an alert may be generated to alert either one of the patient, the attending medical personnel, or both, that the patient has been non-compliant.

Similarly, during monitoring of compliance for ingestion of corticosteroid, for example, if the pacing threshold has not decreased, i.e., the current pacing threshold is not less than the previous determined pacing threshold, NO in Block 406, the device determines the patient non-compliant, Block 408, and a non-compliant indication is generated that is stored, and/or causes an alert to be generated. If an alert is generated to alert the patient, a determination may be made as to whether the patient complies after the alert is generated, as described above.

If the pacing threshold has decreased, i.e., the current pacing threshold is less than the previous determined pacing threshold, YES in Block 406, the device determines whether the change in pacing threshold has been sustained for a predetermined period of time, Block 410, such as 1-3 hours, for example, as described above. Therefore, once the device determines the change in pacing threshold to have occurred, Yes in Block 406, the device determines whether the change in pacing threshold was sustained for a predetermined period of time, such as three hours, for example, Block 410. If the change in pacing threshold is not sustained, i.e., the pacing threshold is determined not to be greater than the pacing threshold for the predetermined period of time, NO in Block 410, the device determines the patient non-compliant, Block 408, and a non-compliant indication is generated that is stored, and/or causes an alert to be generated, as described above. If the change in pacing threshold is sustained, i.e., the pacing threshold is determined to be less than the pacing threshold for the predetermined period of time, YES in Block 410, the device determines the patient to be compliant, Block 410, and waits for the next compliance check, Block 400, to be scheduled to occur, and the process is repeated. An indication that the patient was determined to be either compliant or non-compliant may be stored for later review by the clinical personnel. According to one embodiment, if the patient is determined to be non-compliant, an alert may be generated to alert either one of the patient, the attending medical personnel, or both, that the patient has been non-compliant. If an alert is generated to alert the patient, a determination may be made as to whether the patient complies after the alert is generated, as described above.

Figure 7:
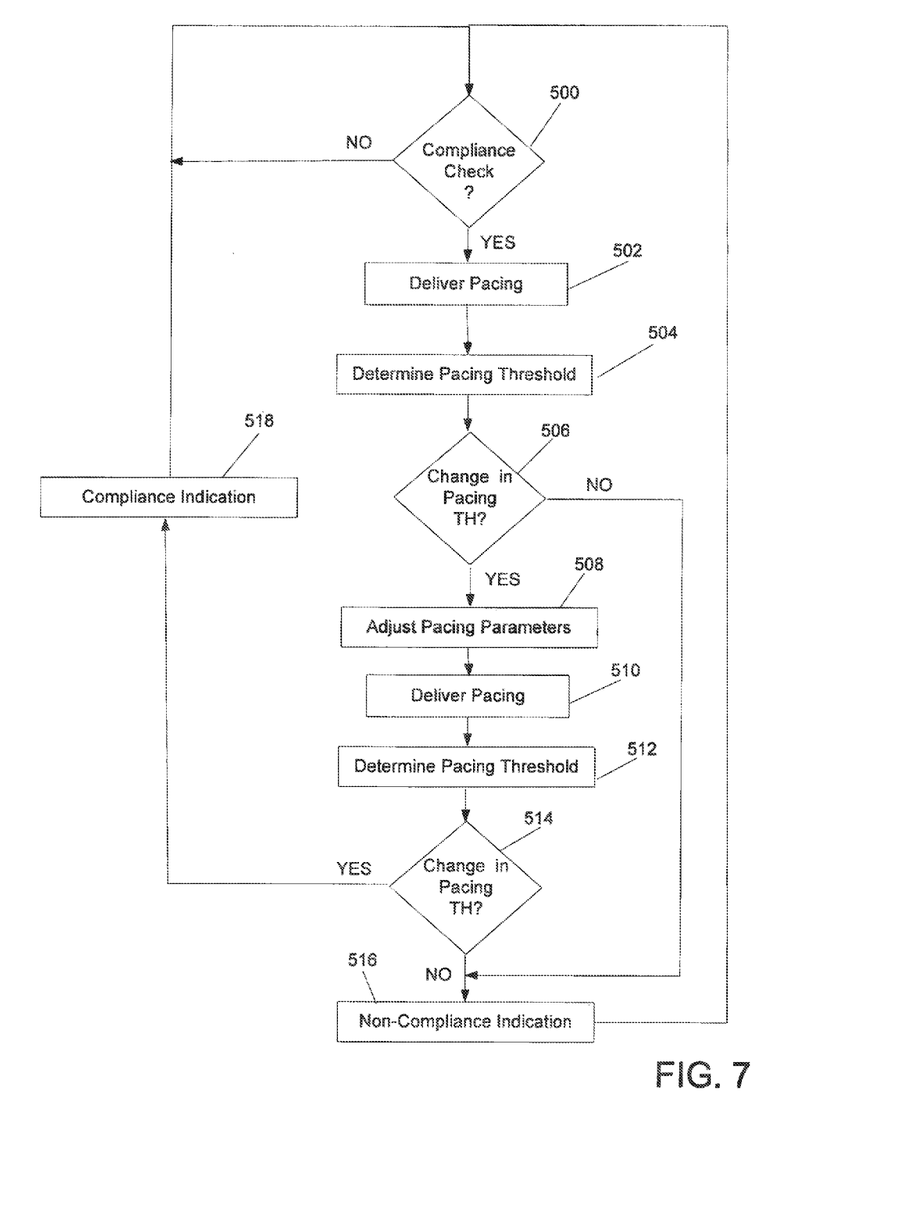
FIG. 7 is a flowchart of an exemplary method for monitoring compliance of a patient medication regimen in a medical device according to an embodiment of the present disclosure.

FIG. 7 is a flowchart of an exemplary method, according to an embodiment of the present disclosure, for monitoring of a patient medication regimen in a medical device. As illustrated in FIG. 7, during monitoring of the device for patient compliance, in order to determine whether to initiate the determination of whether the patient has been compliant with ingestion of medication, the device determines whether it is time to perform the compliance check, Block 500, as described above. Once the compliance check is initiated, YES in Block 500, the device delivers pacing therapy, Block 502, determines a current pacing therapy threshold, Block 504, and based on the current pacing therapy threshold, determines whether there has been a change in the pacing threshold, Block 506. For example, if the device is attempting to determine patient compliance in ingestion of amiodarone, the device determines whether there is an increase in the pacing threshold, Block 506. According to another embodiment, if the device is attempting to determine patient compliance in ingestion of an ace inhibitor, the device determines whether there is a decrease in the pacing threshold, Block 506.

In order to determine whether changes in the pacing threshold are occurring in Block 506, the device determines whether there is either an increase or a decrease in the pacing threshold by comparing the current determined pacing threshold to a prior determined pacing threshold. According to one embodiment, the device determines that a change in the pacing threshold occurs if there is a one-step change in the current adjusted pacing threshold from a prior adjusted pacing threshold determination. According to one embodiment, a one-step increase or decrease in the pacing threshold corresponds to a change of approximately one tenth of a volt, so that, for example, an increase from 0.1 volts to 0.2 volts would correspond to a one-step increase and a decrease from 0.2 volts to 0.1 volts would correspond to a one-step decrease.

During monitoring of compliance for ingestion of amiodarone, for example, the device determines whether an increase in the pacing threshold has occurred. If the pacing threshold has not increased, i.e., the current pacing threshold is not greater than the previous determined pacing threshold, NO in Block 506, the device determines the patient to be non-compliant, Block 516, and a non-compliant indication is generated that is stored, and/or causes an alert to be generated. If the pacing threshold has increased, i.e., the current pacing threshold is greater than the previous determined pacing threshold, YES in Block 506, the device advances to a compliance monitoring mode for monitoring of patient medication compliance.

When in the compliance monitoring mode, Blocks 508-514, the device adjusts delivery of the pacing therapy, Block 508, delivers the adjusted pacing therapy, Block 510, and determines a pacing threshold associated with delivery of the adjusted pacing therapy, Block 512. During adjusting of the pacing therapy, Block 508, the device adjusts one or more of the pacing parameters associated with delivery of the pacing therapy. For example, according to one exemplary embodiment, the device changes the pulse width from 0.5 millisecond utilized during the initial delivery of pacing therapy, Block 502 to a pulse width of 0.06 milliseconds. Once the pacing threshold associated with delivery of the adjusted pacing therapy is determined, Block 512, the device determines whether there has been a change in the pacing threshold in response to delivery of the adjusted pacing therapy, Block 514.

In particular, according to one embodiment of the present disclosure, when monitoring for compliance of ingestion of amiodarone, while in the monitoring compliance mode, the device determines whether there has been a predetermined increase in the pacing threshold during delivery of the adjusted pacing therapy. For example, given the adjusted pacing therapy is delivered having a 0.06 millisecond pulse width, the device determines whether there is a change in pacing threshold between a current determined pacing threshold and a previous determined pacing threshold at the same adjusted pulse width setting, i.e., 0.06 milliseconds. According to an exemplary embodiment of the present disclosure, while in the compliance monitoring mode, in order to determine whether the adjusted pacing threshold change is greater than a change threshold, indicating a change in the pacing threshold during delivery of the adjusted pacing therapy, Block 514, the device determines whether there is a four-step or greater change in the current determined pacing threshold from the previously determined pacing threshold.

If an increase in the pacing threshold is not determined to occur during delivery of the adjusted therapy and therefore there is not a change in the pacing threshold during delivery of the adjusted pacing therapy, NO in Block 514, the device determines the patient to be non-compliant, Block 516, and a non-compliant indication is generated that is stored, and/or causes an alert to be generated. If the pacing threshold has increased, i.e., the current pacing threshold is greater than the previous determined pacing threshold, YES in Block 514, the device determines the patient to be compliant, Block 518, and waits for the next scheduled compliance check, Block 500, and the process is repeated. An indication that the patient was determined to be either compliant Block 518 or non-compliant Block 516 may be stored for later review by the clinical personnel. According to one embodiment, if the patient is determined to be non-compliant, Block 518, an alert may be generated to alert either of the patient, the attending medical personnel, or both, that the patient has been non-compliant.

Similarly, during monitoring of compliance for ingestion of corticosteroid, for example, if the pacing threshold has not decreased, i.e., the current pacing threshold is not less than the previous determined pacing threshold, NO in Block 506, the device determines the patient to be non-compliant, Block 516, and a non-compliant indication is generated that is stored, and/or causes an alert to be generated. If the pacing threshold has decreased, i.e., the current pacing threshold is less than the previous determined pacing threshold, YES in Block 506, the device advances to the compliance monitoring mode, Blocks 508-514, during which the device adjusts delivery of the pacing therapy, Block 508, delivers the adjusted pacing therapy, Block 510, and determines a pacing threshold associated with delivery of the adjusted pacing therapy, Block 512, as described above but with the change in pacing threshold, Blocks 506 and 514, being determined in response to there being a decrease of the pacing threshold.

Once the pacing threshold associated with delivery of the adjusted pacing therapy is determined, the device determines whether there has been a change in the pacing threshold in response to delivery of the adjusted pacing therapy, Block 514. During monitoring of patient compliance for ingestion of corticosteroid, if a decrease in the pacing threshold is not determined to occur during delivery of the adjusted therapy and therefore there is not a change in the pacing threshold during delivery of the adjusted pacing therapy, NO in Block 514, the device determines the patient to be non-compliant, Block 516, and a non-compliant indication is generated that is stored, and/or causes an alert to be generated. If the pacing threshold has decreased, i.e., the current pacing threshold is less than the previous determined pacing threshold, YES in Block 514, the device determines the patient to be compliant, Block 518, and waits for the next scheduled compliance check, Block 500, and the process is repeated. An indication that the patient was determined to be either compliant Block 518 or non-compliant Block 516 may be stored for later review by the clinical personnel. According to one embodiment, if the patient is determined to be non-compliant, Block 518, an alert may be generated to alert either of the patient, the attending medical personnel, or both, that the patient has been non-compliant. If an alert is generated to alert the patient, a determination may be made as to whether the patient complies after the alert is generated, as described above.

Figure 8:
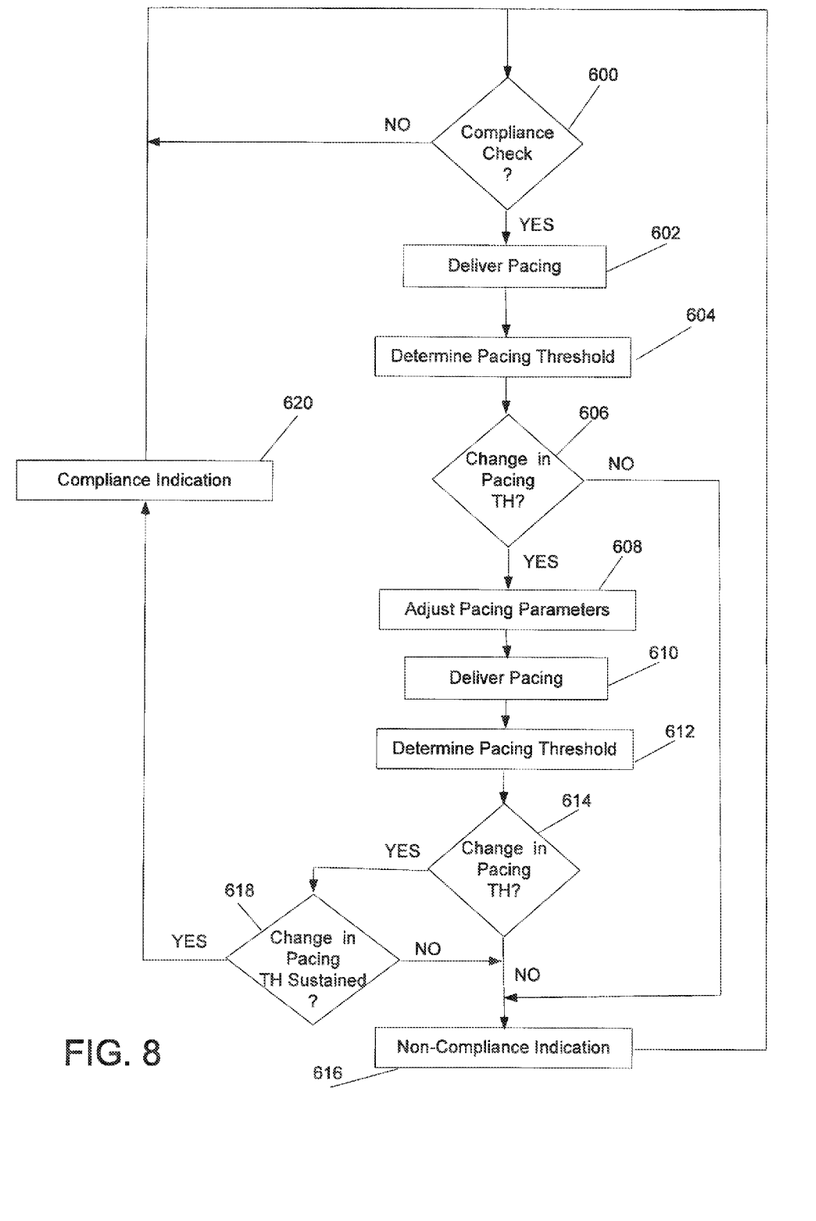
FIG. 8 is a flowchart of an exemplary method for monitoring compliance of a patient medication regimen in a medical device according to an embodiment of the present disclosure.

FIG. 8 is a flowchart of an exemplary method, according to an embodiment of the present disclosure, for monitoring compliance of a patient medication regimen in a medical device. As illustrated in FIG. 8, during monitoring of the device for patient compliance, in order to determine whether to initiate the determination of whether the patient has been compliant with ingestion of medication, the device determines whether it is time to perform the compliance check, Block 600, as described above. Once the compliance check is initiated, YES in Block 600, the device delivers pacing therapy, Block 602, determines a current pacing therapy threshold, Block 604, and based on the current pacing therapy threshold, determines whether there has been a change in the pacing threshold, Block 606. For example, if the device is attempting to determine patient compliance in ingestion of an amiodarone, the device determines whether there is an increase in the pacing threshold, Block 606. According to another embodiment, if the device is attempting to determine patient compliance in ingestion of an ace inhibitor, the device determines whether there is a decrease in the pacing threshold, Block 606.

In order to determine whether changes in the pacing threshold are occurring in Block 606, the device determines whether there is either an increase or a decrease in the pacing threshold by comparing the current determined pacing therapy threshold to a prior determined pacing threshold. According to one embodiment, the device determines that a change in the pacing threshold occurs if there is a one-step change in the current adjusted pacing threshold from a prior adjusted pacing threshold determination. According to one embodiment, a one-step increase or decrease in the pacing threshold corresponds to an increase of approximately one tenth of a volt, so that, for example, an increase from 0.1 volts to 0.2 volts would correspond to a one-step increase and a decrease from 0.2 volts to 0.1 volts would correspond to a one-step decrease.

During monitoring of compliance for ingestion of amiodarone, for example, the device determines whether an increase in the pacing threshold has occurred, Block 606. If the pacing threshold has not increased, i.e., the current pacing threshold is not greater than the previous determined pacing threshold, NO in Block 606, the device determines the patient to be non-compliant, Block 616, and a non-compliant indication is generated that is stored, and/or causes an alert to be generated. If the pacing threshold has increased, i.e., the current pacing threshold is greater than the previous determined pacing threshold, YES in Block 606, the device advances to the compliance monitoring mode for monitoring of patient medication compliance, Blocks 608-614 and 618, during which the device adjusts delivery of the pacing therapy, Block 608, delivers the adjusted pacing therapy, Block 610, and determines a pacing threshold associated with delivery of the adjusted pacing therapy, Block 612.

During adjusting of the pacing therapy, Block 608, the device adjusts one or more of the pacing parameters associated with delivery of the pacing therapy. As described above, ingestion of the medication by the patient will typically cause a change in the pacing threshold to occur for a prolonged period of time, such as three hours for example. Therefore, according to one exemplary embodiment, the device adjusts the pulse width from 0.5 milliseconds utilized during the initial delivery of pacing therapy and delivered once per day at a predetermined time associated when ingestion of the medication is prescribed, i.e., in the morning for example, or twice per day when ingestion of the medication is prescribed twice per day, i.e., morning and evening, Block 602, to a pulse width of 0.6 milliseconds delivered multiple times during the prolonged period of time, i.e., three hours, that ingestion of the medication is expected to cause there to be a change in the pacing threshold. For example, according to one exemplary embodiment, when in the compliance monitoring mode, the pacing therapy is adjusted, Block 608, so as to be delivered, Block 610, at a 0.6 millisecond pulse width once per hour following the initial determined change in the pacing threshold, YES in Block 606, determined prior to the device advancing to the compliance monitoring mode.

Once the pacing threshold associated with delivery of the adjusted pacing therapy is determined, Block 612, the device determines whether there has been a change in the pacing threshold in response to delivery of the adjusted pacing therapy, Block 614. During monitoring of compliance for ingestion of amiodarone, for example, the device determines there has been a change in the pacing threshold by determining whether a predetermined increase in the pacing threshold has occurred. For example, given the adjusted pacing therapy is delivered having a 0.06 millisecond pulse width, the device determines whether there is a change in pacing threshold between a current determined pacing threshold and a previous determined pacing threshold at the same adjusted pulse width setting, i.e., 0.06 milliseconds. According to an exemplary embodiment of the present disclosure, while in the compliance monitoring mode, in order to determine whether the adjusted pacing threshold change is greater than a change threshold, indicating a change in the pacing threshold during delivery of the adjusted pacing therapy, Block 514, the device determines whether there is a four-step or greater change in the current determined pacing threshold from the previously determined pacing threshold.

If an increase in the pacing threshold is not determined to occur during delivery of the adjusted therapy and therefore there is not a change in the pacing threshold during delivery of the adjusted pacing therapy, NO in Block 614, the device determines the patient to be non-compliant, Block 616, and a non-compliant indication is generated that is stored, and/or causes an alert to be generated. If the pacing threshold has increased, i.e., the current pacing threshold is greater than the previous determined pacing threshold, YES in Block 614, the device determines whether the change in pacing threshold has been sustained for a predetermined period of time, Block 618, i.e., three hours, for example. If the change in pacing threshold is not sustained, i.e., the pacing threshold is determined not to be greater than the pacing threshold for the predetermined period of time, NO in Block 618, the device determines the patient to be non-compliant, Block 616, and a non-compliant indication is generated that is stored, and/or causes an alert to be generated. If the change in pacing threshold is sustained, i.e., the pacing threshold is determined to be greater than the pacing threshold for the predetermined period of time, YES in Block 618, the device determines the patient to be compliant, Block 620, and waits for the next scheduled compliance check, Block 600, to occur, and the process is repeated. An indication that the patient was determined to be either compliant, Block 620, or non-compliant, Block 616, may be stored for later review by the clinical personnel. According to one embodiment, if the patient is determined to be non-compliant, Block 616, an alert may be generated to alert either one of the patient, the attending medical personnel, or both, that the patient has been non-compliant.

Similarly, during monitoring of compliance for ingestion of corticosteroid, for example, if the pacing threshold has not decreased, i.e., the current pacing threshold is not less than the previous determined pacing threshold, NO in Block 606, the device determines the patient to be non-compliant, Block 616, and a non-compliant indication is generated that is stored, and/or causes an alert to be generated. If the pacing threshold has decreased, i.e., the current pacing threshold is less than the previous determined pacing threshold, YES in Block 606, the device advances to the compliance monitoring mode, Blocks 608-614 and 618, during which the device adjusts delivery of the pacing therapy, Block 608, delivers the adjusted pacing therapy, Block 610, and determines a pacing threshold associated with delivery of the adjusted pacing therapy, Block 612, as described above.

Once the pacing threshold associated with delivery of the adjusted pacing therapy is determined, the device determines whether there has been a change in the pacing threshold in response to delivery of the adjusted pacing therapy, Block 614, as described above. During monitoring of patient compliance for ingestion of corticosteroid, if a decrease in the pacing threshold is not determined to occur during delivery of the adjusted therapy and therefore there is not a change in the pacing threshold during delivery of the adjusted pacing therapy, NO in Block 614, the device determines the patient to be non-compliant, Block 616, and a non-compliant indication is generated that is stored, and/or causes an alert to be generated. If the pacing threshold has decreased, i.e., the current pacing threshold is less than the previous determined pacing threshold, YES in Block 614, the device determines whether the change in pacing threshold has been sustained for a predetermined period of time, Block 618, as described above. If the change in pacing threshold is not sustained, i.e., the pacing threshold is determined not to be less than the pacing threshold for the predetermined period of time, NO in Block 618, the device determines the patient non-compliant, Block 616, and a non-compliant indication is generated that is stored, and/or causes an alert to be generated. If the change in pacing threshold is sustained, i.e., the pacing threshold is determined to be less than the pacing threshold for the predetermined period of time, YES in Block 618, the device determines the patient to be compliant, Block 620, and waits for the next scheduled compliance check, Block 600, to occur, and the process is repeated. An indication that the patient was determined to be either compliant, Block 620, or non-compliant, Block 616, may be stored for later review by the clinical personnel. According to one embodiment, if the patient is determined to be non-compliant, an alert may be generated to alert either one of the patient, the attending medical personnel, or both, that the patient has been non-compliant. If an alert is generated to alert the patient, a determination may be made as to whether the patient complies after the alert is generated, as described above.

While the method and apparatus for monitoring of patient medication compliance set forth above has been describe within the context of using corticosteroids and anti-arrhythmia medications, such as amiodarone as examples, it is understood that the disclosure is not intended to be limited to monitoring of compliance with respect to only corticosteroids and amioadarone. Rather, any medication that causes changes in the pacing threshold associated with a cardiac device to occur upon ingestion would be intended to be within the scope of the disclosure.

Thus, a medical device system and associated methods for detecting homeostasis variations for monitoring cardiac function have been presented in the foregoing description with reference to specific embodiments. It is understood that the various techniques and devices described may be implemented in any combination. It is appreciated that various modifications to the referenced embodiments may be made without departing from the scope of the disclosure as set forth in the following claims.

The invention claimed is:

1. A medical device for monitoring patient medication compliance, comprising:
a plurality of electrodes to deliver a pacing therapy; and
a processor configured to determine a pacing threshold in response to the delivered pacing therapy, determine whether there is a change in the pacing threshold, and determine patient prescription drug intake compliance in response to the determined changes, wherein the processor is configured to generate an alert in response to the determined patient prescription drug intake compliance, deliver pacing therapy subsequent to generating the alert, determine a pacing threshold in response to the pacing therapy delivered subsequent to generating the alert, determine whether there is a change in the pacing threshold determined in response to the pacing therapy delivered subsequent to generating the alert, and determine patient medication compliance of prescription drug intake in response to determining whether there is a change in the pacing threshold determined in response to the pacing therapy delivered subsequent to generating the alert.

2. The medical device of claim 1, wherein determining whether there is a change in the pacing threshold comprises a one-step change between a current determined pacing threshold and a prior determined pacing threshold.

3. The medical device of claim 1, wherein the processor is configured to determine the patient as being non-compliant in response to determining no change in the pacing threshold and as being compliant in response to determining a change in the pacing threshold.

4. The medical device of claim 1, wherein the patient medication corresponds to amiodarone, and the change corresponds to an increase in the pacing threshold.

5. The medical device of claim 1, wherein the patient medication corresponds to corticosteroid, and the change corresponds to a decrease in the pacing threshold.

6. The medical device of claim 1, further comprising a memory, wherein the processor is configured to one of store the determined patient prescription drug intake compliance in the memory and generate an alert in response to the determined patient medication compliance.

7. The medical device of claim 1, wherein the processor is further configured to determine whether there is a change in the pacing threshold during initial delivery of the pacing therapy, adjust a delivery parameter of the pacing therapy in response to determining the change in the pacing threshold during initial delivery of the pacing therapy, and determine whether there is a change in the pacing threshold during delivery of the adjusted pacing therapy delivered subsequent to the initial delivery of the pacing therapy.

8. The medical device of claim 7, wherein adjusting a delivery parameter of the pacing therapy comprises adjusting a pulse width and a rate of delivery of the pacing therapy.

9. A medical device for monitoring patient medication compliance, comprising:
a plurality of electrodes to deliver a pacing therapy; and
a processor configured to determine a pacing threshold in response to the delivered pacing therapy, determine whether there is a change in the pacing threshold, and determine patient prescription drug intake compliance in response to the determined changes, wherein the processor is further configured to determine whether there is a change in the pacing threshold during initial delivery of the pacing therapy, adjust a delivery parameter of the pacing therapy in response to determining the change in the pacing threshold during initial delivery of the pacing therapy, and determine whether there is a change in the pacing threshold during delivery of the adjusted pacing therapy delivered subsequent to the initial delivery of the pacing therapy, and wherein the determined change in the pacing threshold during initial delivery of the pacing therapy comprises a one-step change and the determined change in the pacing threshold during delivery of the adjusted pacing therapy comprises a four-step increase.

10. The medical device of claim 9, wherein the pulse width is approximately 0.5 milliseconds during initial deliver of the pacing therapy, and the pulse width is approximately 0.06 milliseconds during delivery of the adjusted pacing therapy.

11. A method for monitoring patient medication compliance in a medical device, comprising:
   delivering a pacing therapy;
   determining a pacing threshold in response to the delivered pacing therapy;
   determining whether there is a change in the pacing threshold;
   determining patient prescription drug intake compliance in response to the determined changes in the pacing threshold;
   generating an alert in response to the determined patient prescription drug intake compliance;
   delivering pacing therapy subsequent to generating the alert;
   determining a pacing threshold in response to the pacing therapy delivered subsequent to generating the alert;
   determining whether there is a change in the pacing threshold determined in response to the pacing therapy delivered subsequent to generating the alert; and
   determining patient prescription drug intake compliance in response to determining whether there is a change in the pacing threshold determined in response to the pacing therapy delivered subsequent to generating the alert.

12. The method of claim 11, wherein determining whether there is a change in the pacing threshold comprises a one-step change between a current determined pacing threshold and a prior determined pacing threshold.

13. The method of claim 11, further comprising determining the patient as being non-compliant in response to determining no change in the pacing threshold and as being compliant in response to determining a change in the pacing threshold.

14. The method of claim 11, wherein the patient medication corresponds to amiodarone, and the change corresponds to an increase in the pacing threshold.

15. The method of claim 11, wherein the patient medication corresponds to corticosteroid, and the change corresponds to a decrease in the pacing threshold.

16. The method of claim 11, further comprising one of storing the determined patient prescription drug intake compliance in the memory and generating an alert in response to the determined patient medication compliance.

17. The method of claim 11, further comprising:
   determining whether there is a change in the pacing threshold during initial delivery of the pacing therapy;
   adjusting a delivery parameter of the pacing therapy in response to determining the change in the pacing threshold during initial delivery of the pacing therapy; and
   determining whether there is a change in the pacing threshold during delivery of the adjusted pacing therapy delivered subsequent to the initial delivery of the pacing therapy.

18. The method of claim 17, wherein adjusting a delivery parameter of the pacing therapy comprises adjusting a pulse width and a rate of delivery of the pacing therapy.

19. A method for monitoring patient medication compliance in a medical device, comprising:
   delivering a pacing therapy;
   determining a pacing threshold in response to the delivered pacing therapy;
   determining whether there is a change in the pacing threshold;
   determining patient prescription drug intake compliance in response to the determined changes in the pacing threshold;
   determining whether there is a change in the pacing threshold during initial delivery of the pacing therapy;
   adjusting a delivery parameter of the pacing therapy in response to determining the change in the pacing threshold during initial delivery of the pacing therapy; and
   determining whether there is a change in the pacing threshold during delivery of the adjusted pacing therapy delivered subsequent to the initial delivery of the pacing therapy, wherein the determined change in the pacing threshold during initial delivery of the pacing therapy comprises a one-step change and the determined change in the pacing threshold during delivery of the adjusted pacing therapy comprises a four-step increase.

20. The method of claim 19, wherein the pulse width is approximately 0.5 milliseconds during initial deliver of the pacing therapy, and the pulse width is approximately 0.06 milliseconds during delivery of the adjusted pacing therapy.

21. A non-transitory computer-readable medium for storing a set of instructions for performing a method, the method comprising:
   delivering a pacing therapy;
   determining a pacing threshold in response to the delivered pacing therapy;
   determining whether there is a change in the pacing threshold;
   determining patient prescription drug intake compliance in response to the determined changes in the pacing threshold;
   generating an alert in response to the determined patient prescription drug intake compliance;
   delivering pacing therapy subsequent to generating the alert;
   determining a pacing threshold in response to the pacing therapy delivered subsequent to generating the alert;
   determining whether there is a change in the pacing threshold determined in response to the pacing therapy delivered subsequent to generating the alert; and
   determining patient prescription drug intake compliance in response to determining whether there is a change in the pacing threshold determined in response to the pacing therapy delivered subsequent to generating the alert.

* * * * *